(12) United States Patent
Schutz

(10) Patent No.: US 10,119,949 B1
(45) Date of Patent: Nov. 6, 2018

(54) TEMPLATE FOR MEASURING AND QUANTIFYING DEFECTS IN PRODUCE

(71) Applicant: Denver Floyd Schutz, Reedley, CA (US)

(72) Inventor: Denver Floyd Schutz, Reedley, CA (US)

(73) Assignee: GERAWAN FARMING, INC, Fresno, CA (US)

( * ) Notice: Subject to any disclaimer, the term of this patent is extended or adjusted under 35 U.S.C. 154(b) by 145 days.

(21) Appl. No.: 15/443,149

(22) Filed: Feb. 27, 2017

Related U.S. Application Data

(60) Provisional application No. 62/338,975, filed on May 19, 2016.

(51) Int. Cl.
*G01B 3/14* (2006.01)
*G01N 33/02* (2006.01)
*G01B 3/02* (2006.01)
*G01N 21/88* (2006.01)

(52) U.S. Cl.
CPC ............ *G01N 33/025* (2013.01); *G01B 3/02* (2013.01); *G01N 21/8803* (2013.01)

(58) Field of Classification Search
CPC .................................................. G01N 33/025
USPC ................................................. 33/1 BB, 503
See application file for complete search history.

(56) References Cited

U.S. PATENT DOCUMENTS

| | | | | |
|---|---|---|---|---|
| 1,814,401 A * | 7/1931 | Morrell | ................... | B07B 13/00 33/561.2 |
| 2,277,037 A * | 3/1942 | Clark | ..................... | G01N 29/12 209/599 |
| 3,071,171 A * | 1/1963 | Guerrero | ................. | A47J 17/00 24/20 EE |
| 5,811,680 A * | 9/1998 | Galili | ....................... | G01N 3/38 73/12.01 |
| 6,435,002 B1 * | 8/2002 | Briggs | ................. | G01N 33/025 422/82.09 |
| 8,601,707 B2 * | 12/2013 | Meritt | ...................... | G01B 3/10 33/494 |
| 2001/0045517 A1 * | 11/2001 | Iida | .................... | G01N 21/3563 250/339.06 |
| 2013/0333454 A1 * | 12/2013 | Benedetti | ................ | G01N 3/30 73/81 |
| 2014/0360037 A1 * | 12/2014 | DeLucia | .................. | G01B 7/12 33/555.4 |
| 2015/0319929 A1 * | 11/2015 | Hendrickson | ........ | A01D 45/025 33/504 |
| 2018/0209901 A1 * | 7/2018 | Schwartzer | ........ | G01N 21/3563 |

* cited by examiner

*Primary Examiner* — G. Bradley Bennett
(74) *Attorney, Agent, or Firm* — Plager Schack LLP; Mark H. Plager; Kara Verryt

(57) ABSTRACT

A tool for measuring and quantifying defects in produce includes a template; at least one graphic indicia printed on the template, the graphic indicia providing a pictorial sample of a specific tolerance for a specific quality defect in the produce; and at least one textual description printed on the template proximate to the graphic indicia, the at least one textual description providing a written description of the specific tolerance.

7 Claims, 3 Drawing Sheets

TEMPLATE FOR MEASURING AND QUANTIFYING DEFECTS IN PRODUCE

RELATED APPLICATION

This application claims priority to provisional patent application U.S. Ser. No. 62/338,975 filed on May 19, 2016 entire contents of which is herein incorporated by reference.

BACKGROUND

The embodiments herein relate generally to quality control of produce, and more particularly, to template for measuring and quantifying defects in produce.

Quality control of produce, particularly stone fruit, is important to ensuring that the consumer is receiving produce that meets certain criteria. However, without a physical and objective measuring and reference device, quality control employees must rely on visualization and recall, each of which are imprecise and unreliable reference authorities. But, no physical and objective measuring and reference device currently exists. Existing devices include a circle template. However, these templates do not include pictorial samples or information on specific tolerances for defects. Thus, conventional methods and devices result in less than ideal grading and separation of produce based on overall quality.

Therefore, what is needed is a template for measuring and quantifying defects in produce.

SUMMARY

Some embodiments of the present disclosure include a tool for measuring and quantifying defects in produce. The tool may include a template; at least one graphic indicia printed on the template, the graphic indicia providing a pictorial sample of a specific tolerance for a specific quality defect in the produce; and at least one textual description printed on the template proximate to the graphic indicia, the at least one textual description providing a written description of the specific tolerance.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used to measure and quantify defects in produce and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

1. Semi-Transparent Template
2. Scale
3. Evaluation Cells
4. Graphic Indicia
5. Text Description The various elements of the device of the present disclosure may be related in the following exemplary fashion. It is not intended to limit the scope or nature of the relationships between the various elements and the following examples are presented as illustrative examples only.

Figure 1:
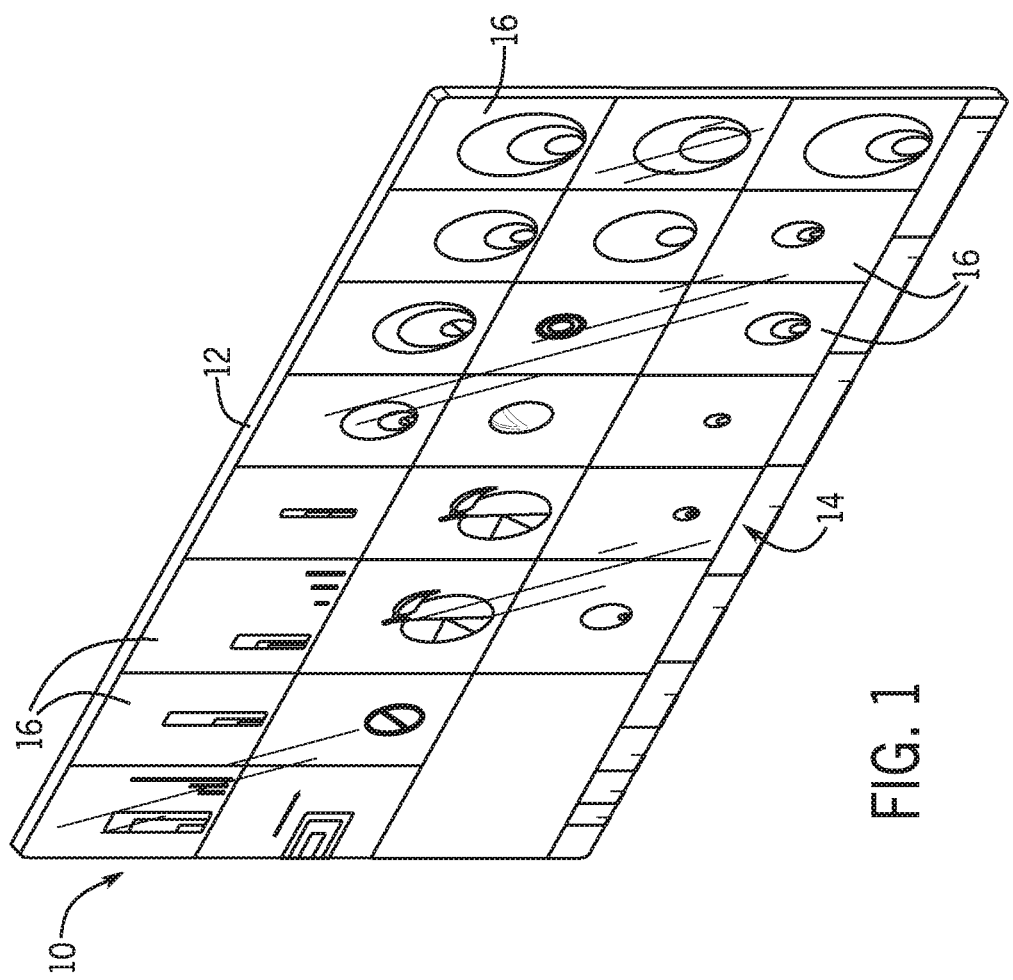
FIG. 1 is a perspective view of one embodiment of the present disclosure.
Figure 2A:
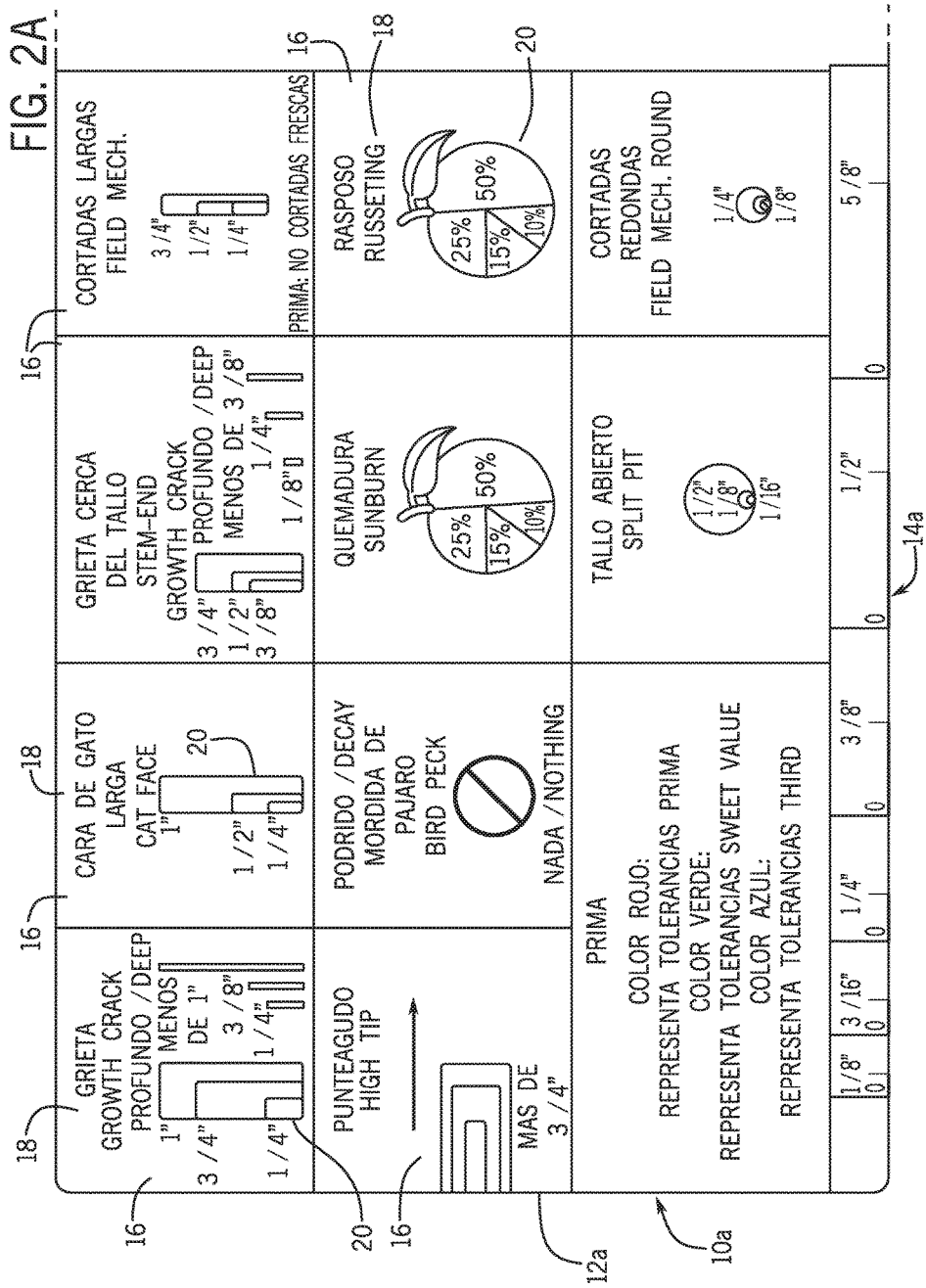
FIG. 2A is a front elevation view of one half of one embodiment of the present disclosure.
Figure 2B:
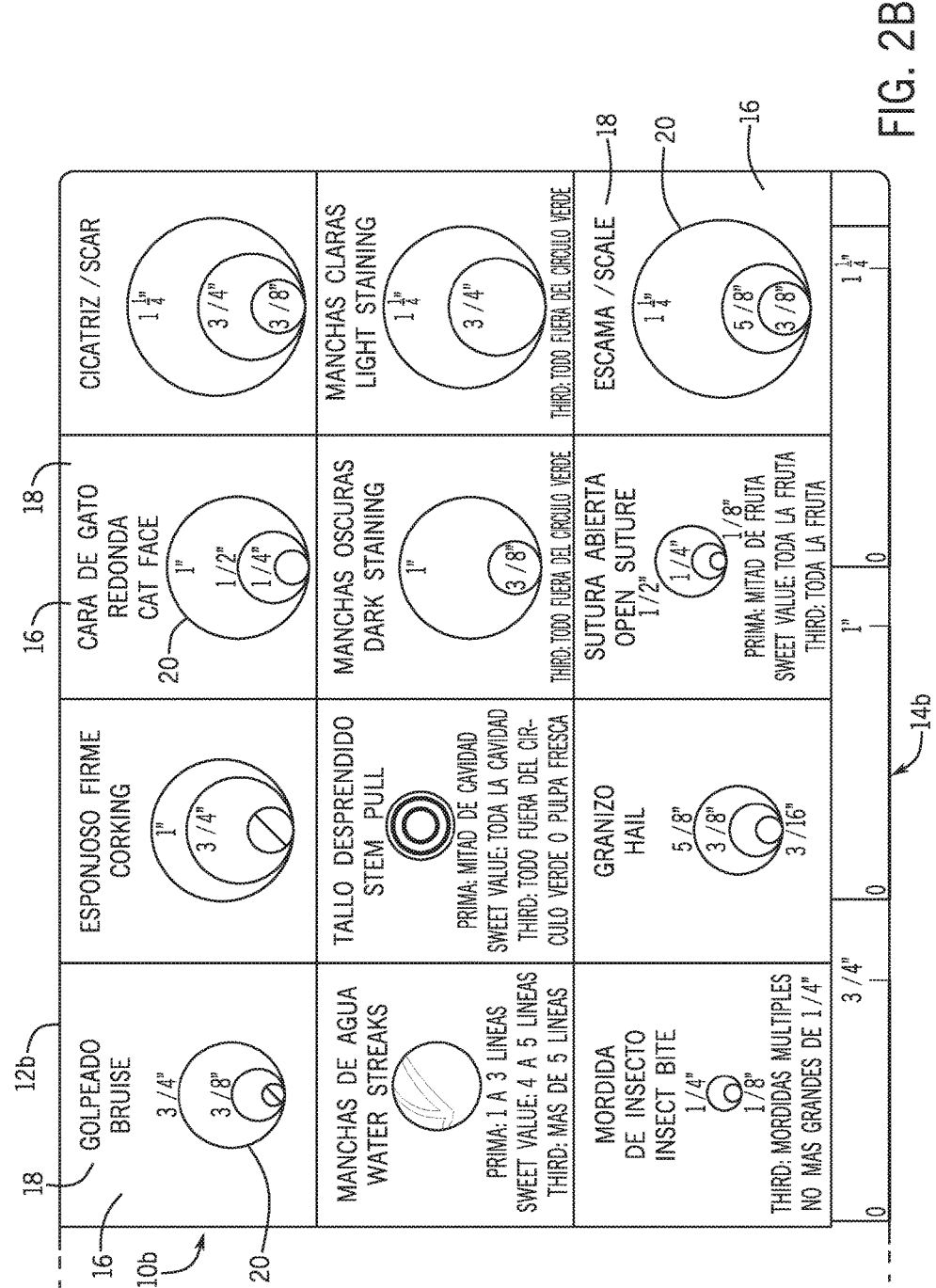
FIG. 2B is a front elevation view of a second half of one embodiment of the present disclosure.

By way of example, and referring to FIGS. 1-2B, some embodiments of the present disclosure include a tool 10 for measuring and quantifying defects in produce, the tool comprising a template 12, such as a semi-transparent template; at least one graphic indicia 20 printed on the template 12, the graphic indicia 20 providing a pictorial sample of a specific tolerance for a specific quality defect in the produce; and at least one textual description 18 printed on the template 12 proximate to the graphic indicia 20, the at least one textual description 18 providing a written description of the specific tolerance. The tool 10 may further comprise a scale 14 printed on a surface of the template 12, wherein the scale 14 displays precise measurement indicators to enable a user to precisely measure defects on the produce.

In embodiments, a single template 12 may comprise graphic indicia 20 and textual descriptions 18 for a plurality of defects. As shown in FIGS. 1-2A, the defects may be arranged in a plurality of evaluation cells 16, wherein each evaluation cell 16 includes a graphic indicia 20 and textual description 18 for a specific defect.

In a specific example, the tool 10 may be used for quality control of stone fruit. As shown in the Figures, the defects designed to be measured and quantified by the tool 10 may include growth crack, cat face, stem-end growth crack, field mech., bruise, corking, scar, high tip, decay/bird peck, sunburn, russeting, water streaks, stem pull, dark staining, light staining, split pit, field mech. round, insect bite, hail, open suture, and scale, all of which are defined according to their ordinary meaning in the stone fruit industry. A specific example of the template 12 for measuring these defects is shown in FIGS. 2A and 2B, wherein FIG. 2A shows a first half 10a of the tool (and thus a first half 12a of the template 12 and a first half 14a of the scale 14) and FIG. 2B shows a second half 10b of the tool (and thus a second half 12b of the template 12 and a second half 14b of the scale 14).

While not shown in color, the tool 10 of the present disclosure may include multiple colors to help quantify and measure defects. For example, in the tool shown in FIGS. 2A and 2B, the largest values may be printed in a blue ink, to represent a third tolerance; the medium values may be printed in a green ink to indicate a "sweet value"; and the smallest values may be printed in a red ink to indicate a "Prima" value, wherein the Prima value may be the acceptable value for defects for a given produce company, and the sweet value and third tolerance may be unacceptable defects for a given produce company. For example, the growth crack evaluation cell 16 may include three rectangular graphic indicia 20, wherein the largest is labeled 1" and is printed in blue ink, the middle is labeled ¾" and printed in green ink, and the smallest is labeled ¼" and labeled in red ink. For a particular produce company, a user would easily determine that only the red ink (i.e., ¼" growth crack) may be acceptable. While the red, green, and blue colors are used and described above, other colors or varying lines may be used to distinguish between suitable vs. not suitable defects. For example, instead of changing the color of the graphic indicia 20 and the text description 18, the graphic indicia 20 may use different types of dashed lines and the text description 18 may use different fonts. This alternate version may be particularly helpful in the case of a colorblind user.

As shown in the Figures, the tool 10 may include text descriptions 18 in multiple languages such that the tool 10 may be used by a large number of individuals.

While the Figures show a tool 10 used to measure stone fruit, other tools 10 may include templates and quality control information for other types of produce.

To use the tool 10 of the present disclosure, the user may simply hold the template 12 up to the piece of produce to visually measure and quantify any defects. Based on the specifications indicated on the template 12, the user may easily determine whether the produce meets quality control standards and may easily grade and separate produce based on quality.

The tool 10 of the present disclosure may be made from any suitable material and, in some embodiments, comprises a layered construction comprising the graphic indicia 20 and the textual descriptions 18 printed on a transparent printing sheet, which is then laminated between two laminating sheets having a thickness of, for example, about 10 mil. The tool 10 may then be cut to form, if necessary.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A tool for measuring and quantifying defects in produce, the tool comprising:
    a template;
    at least one graphic indicia printed on the template, the graphic indicia providing a pictorial sample of a specific tolerance for a specific quality defect in the produce; and
    at least one textual description printed on the template proximate to the graphic indicia, the at least one textual description providing a written description of the specific tolerance.

2. The tool of claim 1, further comprising a scale printed on a surface of the template, wherein the scale displays precise measurement indicators.

3. The tool of claim 1, wherein the template comprises graphic indicia and textual descriptions for a plurality of specific tolerance and specific quality defects.

4. The tool of claim 3, wherein:
    the template comprises a plurality of evaluation cells; and
    each evaluation cell includes a graphic indicia and textual description for a specific defect.

5. The tool of claim 1, wherein:
    the produce is stone fruit; and
    the specific quality defect is a member selected from the group consisting of growth crack, cat face, stem-end growth crack, field mech., bruise, corking, scar, high tip, decay/bird peck, sunburn, russeting, water streaks, stem pull, dark staining, light staining, split pit, field mech. round, insect bite, hail, open suture, and scale.

6. The tool of claim 1, wherein:
    the produce is stone fruit; and
    the template includes a graphic indicia and a textual description for each of the following specific quality defects:
    growth crack,
    cat face,
    stem-end growth crack,
    field mech,
    bruise,
    corking,
    scar,
    high tip,
    decay/bird peck,
    sunburn,
    russeting,
    water streaks,
    stem pull,
    dark staining,
    light staining,
    split pit,
    field mech. round,
    insect bite,
    hail,
    open suture, and
    scale.

7. The tool of claim 1, wherein varying grades for the specific tolerances are displayed in different colors to help quantify and measure the specific defects.

\* \* \* \* \*